(12) United States Patent
Gu et al.

(10) Patent No.: US 10,639,399 B2
(45) Date of Patent: May 5, 2020

(54) CONSTRUCTION OF MICRORNA GENE-MEDIATED NOVEL TISSUE ENGINEERED NERVE AND APPLICATIONS THEREOF IN REPAIRING NERVE DEFECT

(71) Applicant: NANTONG UNIVERSITY, Nantong, Jiangsu (CN)

(72) Inventors: Xiaosong Gu, Jiangsu (CN); Fei Ding, Jiangsu (CN); Xin Tang, Jiangsu (CN); Yumin Yang, Jiangsu (CN); Bin Yu, Jiangsu (CN); Shiying Li, Jiangsu (CN); Songlin Zhou, Jiangsu (CN); Luzhong Zhang, Jiangsu (CN); Yaxian Wang, Jiangsu (CN); Yun Gu, Jiangsu (CN); Hualin Sun, Jiangsu (CN)

(73) Assignee: NANTONG UNIVERSITY, Nantong, Jiangsu (CN)

( * ) Notice: Subject to any disclaimer, the term of this patent is extended or adjusted under 35 U.S.C. 154(b) by 0 days.

(21) Appl. No.: 16/089,190

(22) PCT Filed: Apr. 5, 2017

(86) PCT No.: PCT/CN2017/079408
§ 371 (c)(1),
(2) Date: Sep. 27, 2018

(87) PCT Pub. No.: WO2018/090542
PCT Pub. Date: May 24, 2018

(65) Prior Publication Data
US 2019/0111179 A1 Apr. 18, 2019

(30) Foreign Application Priority Data
Nov. 21, 2016 (CN) .......................... 2016 1 1043367

(51) Int. Cl.
| | | |
|---|---|---|
| C07H 21/04 | (2006.01) | |
| A61L 27/36 | (2006.01) | |
| A61L 27/56 | (2006.01) | |
| A61L 27/54 | (2006.01) | |
| A61L 27/24 | (2006.01) | |
| A61L 27/22 | (2006.01) | |
| C12N 15/113 | (2010.01) | |

(52) U.S. Cl.
CPC ........... *A61L 27/3675* (2013.01); *A61L 27/22* (2013.01); *A61L 27/24* (2013.01); *A61L 27/3687* (2013.01); *A61L 27/54* (2013.01); *A61L 27/56* (2013.01); *C12N 15/113* (2013.01); *A61L 2300/412* (2013.01); *A61L 2430/32* (2013.01); *C12N 2310/113* (2013.01); *C12N 2310/141* (2013.01); *C12N 2320/32* (2013.01)

(58) Field of Classification Search
None
See application file for complete search history.

(56) References Cited

U.S. PATENT DOCUMENTS

2005/0261218 A1\* 11/2005 Esau ...................... C12N 15/111
514/44 A

FOREIGN PATENT DOCUMENTS

| CN | 1589913 A | 3/2005 |
|---|---|---|
| CN | 102307593 A | 1/2012 |
| CN | 102343114 A | 2/2012 |
| CN | 103041450 A | 4/2013 |
| CN | 103656623 A | 3/2014 |
| CN | 103933582 A | 7/2014 |
| CN | 106474549 A | 3/2017 |
| JP | 2014533248 A | 12/2014 |

OTHER PUBLICATIONS

Yi, Sheng et al., "Regulatory Effect of MicroRNAs on Peripheral Nerve Regeneration", Acta Antomica Sinica, vol. 47, No. 3, Jun. 2016, 425-428.
Gu, Xiaosong et al., "Neural Tissue Engineering Options for Peripheral Nerve Regeneration", Biomaterials, vol. 35, May 10, 2014 (May 10, 2014), 6143-6156.
Zuo, Qiao et al., "Specific Expression of MicroRNA in Different Tissues of Nervous System and Expression Changes in Nerve Regeneration", Progress in Physiological Sciences, vol. 42, No. 2, 2011, 261-268.
Gu, Xiaosong, "Progress and Perspectives of Neural Tissue Engineering", Front. Med., 9(4), Dec. 31, 2015 (Dec. 31, 2015), 401-411.
Zhou, Songlin et al., "miR-9 Inhibits Schwann Cell Migration by Targeting Cthrc1 Following Sciatic Nerve Injury", Journal of Cell Science, vol. 127, Dec. 31, 2014 (Dec. 31, 2014), 967-976.

(Continued)

*Primary Examiner* — Kimberly Chong
(74) *Attorney, Agent, or Firm* — Novick, Kim & Lee, PLLC; Allen Xue

(57) ABSTRACT

Provided is a use of one or more MicroRNA genes selected from miRNAs of Family Let-7, miR-21 or miR-222 in the construction of tissue engineered nerves and in the repair of peripheral nerve defects. An outer and/or internal surface or pores of a tissue engineered nerve graft are coated or adsorbed with polymeric nanomicrospheres carrying a Let-7 family miRNA inhibitor, miR-21, or miR-222, or a mimetic thereof, wherein the polymeric material is composed of biocompatible fibronectin and heparin. The regeneration of peripheral nerves and the construction of tissue engineered nerves are promoted by regulating the expression of MicroRNA genes which can effectively promote the proliferation of primary Schwann cells cultured in vitro and have an anti-apoptotic effect on neuronal cells. In-vivo test proves that bridging of the tissue engineered nerve graft can facilitate the regeneration of peripheral nerves, thus being useful in the treatment of peripheral nerve injury.

9 Claims, 4 Drawing Sheets

Specification includes a Sequence Listing.

(56) References Cited

OTHER PUBLICATIONS

Christie, K.J. et al., "PTEN Inhibition to Facilitate Intrinsic Regenerative Outgrowth of Adult Peripheral Axons", The Journal of Neuroscience, 30(27), Jul. 7, 2010 (Jul. 7, 2010), 9306-9315.

Jianyong Wang et al., "MicroRNA-338 and microRNA-21 co-transfection for the treatment of rat sciatic nerve injury", Neurol Science, 2016, vol. 37, p. 883-890.

Shiying Li et al., "Let-7 microRNAs Regenerate Peripheral Nerve Regeneration by Targeting Nerve Growth Factor", Molecular Therapy, Mar. 2015 vol. 23, No. 3, pp. 423-433.

\* cited by examiner

A

B

C

D

E

F

SEQUENCE LISTING

```
<160> NUMBER OF SEQ ID NOS: 14

<210> SEQ ID NO 1
<211> LENGTH: 22
<212> TYPE: RNA
<213> ORGANISM: Artificial sequence
<220> FEATURE:
<223> OTHER INFORMATION: synthesized

<400> SEQUENCE: 1
ugagguagua gguuguauag uu                                           22

<210> SEQ ID NO 2
<211> LENGTH: 22
<212> TYPE: RNA
<213> ORGANISM: Artificial sequence
<220> FEATURE:
<223> OTHER INFORMATION: synthesized

<400> SEQUENCE: 2
cuauacaauc uacugucuuu cc                                           22

<210> SEQ ID NO 3
<211> LENGTH: 22
<212> TYPE: RNA
<213> ORGANISM: Artificial sequence
<220> FEATURE:
```

-continued

```
<223> OTHER INFORMATION: synthesized

<400> SEQUENCE: 3
ugagguagua gguugugugg uu                                              22

<210> SEQ ID NO 4
<211> LENGTH: 22
<212> TYPE: RNA
<213> ORGANISM: Artificial sequence
<220> FEATURE:
<223> OTHER INFORMATION: synthesized

<400> SEQUENCE: 4
cuauacaacc uacugccuuc cc                                              22

<210> SEQ ID NO 5
<211> LENGTH: 22
<212> TYPE: RNA
<213> ORGANISM: Artificial sequence
<220> FEATURE:
<223> OTHER INFORMATION: synthesized

<400> SEQUENCE: 5
ugagguagua gguuguaugg uu                                              22

<210> SEQ ID NO 6
<211> LENGTH: 22
<212> TYPE: RNA
<213> ORGANISM: Artificial sequence
<220> FEATURE:
<223> OTHER INFORMATION: synthesized

<400> SEQUENCE: 6
cuguacaacc uucuagcuuu cc                                              22

<210> SEQ ID NO 7
<211> LENGTH: 22
<212> TYPE: RNA
<213> ORGANISM: Artificial sequence
<220> FEATURE:
<223> OTHER INFORMATION: synthesized

<400> SEQUENCE: 7
agagguagua gguugcauag uu                                              22

<210> SEQ ID NO 8
<211> LENGTH: 22
<212> TYPE: RNA
<213> ORGANISM: Artificial sequence
<220> FEATURE:
<223> OTHER INFORMATION: synthesized

<400> SEQUENCE: 8
cuauacgacc ugcugccuuu cu                                              22

<210> SEQ ID NO 9
<211> LENGTH: 22
<212> TYPE: RNA
<213> ORGANISM: Artificial sequence
<220> FEATURE:
<223> OTHER INFORMATION: synthesized

<400> SEQUENCE: 9
ugagguagua aguuguauug uu                                              22
```

```
<210> SEQ ID NO 10
<211> LENGTH: 21
<212> TYPE: RNA
<213> ORGANISM: Artificial sequence
<220> FEATURE:
<223> OTHER INFORMATION: synthesized

<400> SEQUENCE: 10
cuauacaacu uacuacuuuc c                                              21

<210> SEQ ID NO 11
<211> LENGTH: 22
<212> TYPE: RNA
<213> ORGANISM: Artificial sequence
<220> FEATURE:
<223> OTHER INFORMATION: synthesized

<400> SEQUENCE: 11
uagcuuauca gacugauguu ga                                             22

<210> SEQ ID NO 12
<211> LENGTH: 22
<212> TYPE: RNA
<213> ORGANISM: Artificial sequence
<220> FEATURE:
<223> OTHER INFORMATION: synthesized

<400> SEQUENCE: 12
caacagcagu cgaugggcug uc                                             22

<210> SEQ ID NO 13
<211> LENGTH: 21
<212> TYPE: RNA
<213> ORGANISM: Artificial sequence
<220> FEATURE:
<223> OTHER INFORMATION: synthesized

<400> SEQUENCE: 13
ggcucaguag ccaguguaga u                                              21

<210> SEQ ID NO 14
<211> LENGTH: 21
<212> TYPE: RNA
<213> ORGANISM: Artificial sequence
<220> FEATURE:
<223> OTHER INFORMATION: synthesized

<400> SEQUENCE: 14
agcuacaucu ggcuacuggg u                                              21
```

CONSTRUCTION OF MICRORNA GENE-MEDIATED NOVEL TISSUE ENGINEERED NERVE AND APPLICATIONS THEREOF IN REPAIRING NERVE DEFECT

INCORPORATION OF SEQUENCE LISTING

This application contains a sequence listing submitted in Computer Readable Form (CRF). The CFR file containing the sequence listing entitled "7-PA440-0002-SequenceListing.txt", which was created on Jun. 19, 2018 and was modified on Jul. 6, 2018, and is 2,376 bytes in size. The information in the sequence listing is incorporated herein by reference in its entirety.

BACKGROUND

Technical Field

The present invention relates to the technical field of biomedicines, and in particular to use of MicroRNA genes in the construction of tissue engineered nerves and in the repair of nerve defects.

Related Art

Peripheral nerve injury is a common clinical disease that is caused by traffic accidents and a variety of accidental injuries and is on a sharp rise. With the rapid development of China's economy, the number of patients with peripheral nerve injury caused by traffic and production accidents and other accidental traumas also increases year by year. At present, there are nearly 20 millions of patients suffering from dysfunction after peripheral nerve injury in China, with the increase rate being nearly 2 millions of patients per year. Peripheral nerve injury has serious impact on the quality of life of patients, and the loss of labor power and the increase in medical expenses cause serious burdens to the society.

Peripheral nerve injury often leads to paralysis, palsy and loss of autonomous control over corresponding body area. The effect of surgical repair of the nerve injury is currently less desirable. There is a need for new strategies to improve specific axonal regeneration after nerve injury. Neurons of the peripheral nervous system have higher intrinsic regeneration ability than the neurons of the central nervous system, and can regenerate axons under suitable environmental conditions. The peripheral nerve regeneration process is complex and controlled by multiple factors. Good microenvironment is conducive to the nerve regeneration.

Autologous nerve transplantation has been accepted as a gold standard for repairing peripheral nerve defects. However, because the autogenous nerve donor is hardly available, transplantation often causes secondary damage, and thus the application is greatly limited. The bridging and transplantation of xenograft are limited in the clinical application, because the allogeneic or heterogeneous tissue may carry the source of infection per se and thus easily lead to infectious diseases, and immune rejection also exists.

At present, the research direction of autologous nerve replacements is mainly toward tissue engineered nerve. The tissue engineered nerve is usually composed of a scaffold, an extracellular matrix, seed cells, growth factors and others. To better guide the growth of nerve tissue, a hollow neural tube is added with a fibrous scaffold, a gel or prepared into a neural tube having a number of microchannels. Studies confirm that compared with an unfilled hollow neural tube, an artificial nerve graft with such improvements is increased in terms of the distance to repair the nerve defects. On the basis of biological nerve grafts, other researchers have a specific extracellular matrix or growth factors incorporated to enhance the repair function. Studies show that the tissue-engineered nerves can help the organism produce a microenvironment favorable to regeneration locally in the site of injury.

The neural tubes simply made of scaffold materials, such as collagen, chitosan, polyglycolic acid and other materials are neural tubes of artificially synthesized and natural materials that are initially used in the repair of peripheral nerve defects, and some products have been commercialized and approved for clinical use. However, the products have limited ability to repair defects, and generally can only be used to repair short-distance peripheral nerve defects. Schwann cells and bone marrow mesenchymal stem cells used as seed cells are hardly available because they can be obtained only after secondary injury, and also have the problem of immunogenicity and others. The growth factors added to the scaffold material are also problematic in maintaining their stability and efficiency. In the method where an extracellular matrix is incorporated on the basis of biological nerve graft to enhance the repair function, the cells need to be co-incubated with the neural tube in vitro. The period is long, the steps are cumbersome, and decellularization is needed in a later time to remove the immunogenicity. It is difficult to ensure the consistency between batches MicroRNAs (miRNA) are a class of endogenous small non-coding single-stranded RNAs (less than 22 nucleotides in length) that are widely present in eukaryotes and negatively regulate the post-translational expression of proteins by inhibiting the protein translation or degrading a target mRNA. MiRNAs are a wide range of regulatory factors present during development and cell differentiation.

The lethal-7 (let-7) family of microRNAs is first found in *C. elegans*, and is highly conserved in vertebrates and nonvertebrates. The Let-7 family of microRNAs can regulate the neuronal cell fate, and have effect on neurodegenerative diseases and nerve regeneration. The 8 members let-7a, 7b, 7c, 7c, 7d, 7e, 7f, 7i and miR-98 in the family have substantially the same expression at various times after sciatic nerve injury, and the variation in expression is negatively correlated with NGF. The Let-7 family of microRNAs significantly reduces the proliferation and migration of primary Schwann cells cultured in vitro by directly targeting and regulating NGF and reducing the protein translation of NGF. After sciatic nerve injury, the Schwann cell is promoted to secrete NGF and the axon co-cultured with Schwann cells and DRG neurons is promoted to grow by inhibiting the expression of Let-7 microRNAs. In vivo animal experiments show that inhibition on Let-7 MicroRNA expression contributes to the migration of Schwann cells and the axon growth in a regeneration microenvironment.

The miR-21 gene is located on chromosome 17q23.2, which is widely present in the tissues and organs of mammals. The miR-21 gene is a proto-oncogene, and highly expressed in almost all human cancers. Approximately two-thirds of the experimental results show that the miR-21 gene is associated with endogenous/exogenous apoptosis. MiR-222 is located on chromosome Xp11.3, and its expression is up-regulated in many patients with cancer in clinic.

After sciatic nerve injury, miR-21 and miR-222 reduce the apoptosis of neurons in the dorsal root ganglion in adult rats by inhibiting the expression of tissue inhibitor of metalloproteinase 3 (TIMP3). MiR-21 and miR-222 directly target the super-apoptotic protein TIMP3. MiR-21 and miR-222 are among the 13 miRNA genes differentially expressed in the L4-6 dorsal root ganglia during the first 7 days after sciatic nerve transection in rats. The expression of miR-21 and miR-222 is continuously increased within 7 days after injury. Over-expression of miR-21 and miR-222 significantly inhibits the apoptosis of neurons in dorsal root ganglion cultured in vitro, increases the viability of neurons in dorsal root ganglion and promotes the growth of neuronal processes by their effect of inhibiting and targeting TIMP3. After sciatic nerve injury, miR-21 is highly expressed in the spinal and dorsal root ganglia, and promotes the growth of neurite by directly targeting and down-regulating the expression of Sprouty2 protein.

The addition of a microRNA-222 inhibitor to DRG neurons cultured in-vitro can inhibit the growth of neurite. Phosphatase and tensin homolog (PTEN) is a gene that is directly targeted by microRNA-222. PTEN is an important regulator inhibiting nerve regeneration, and inhibition of PTEN can increase the intrinsic regeneration ability of adult peripheral axon. MiR-222 regulates the phosphorylation of cAMP response element binding protein (CREB) by PTEN. The activation of c-Jun increases the expression of miR-222 and regulates and activates the intrinsic regeneration ability of neurons after peripheral nerve injury at the transcriptional level. MiR-222 is a proto-oncogene directly targeting TIMP3 and PTEN, and is associated with the tumor necrosis factor (TNF)-induced signaling pathways.

So far, there is no research in which local microRNA expression for regulating the body damage is combined with the construction of novel tissue-engineered nerves to promote nerve regeneration and repair peripheral nerve defects.

SUMMARY

The present invention is designed according to the theoretical characteristics of peripheral nerve regeneration, in which regulation of the expression of miRNAs belonging to the Family Let-7, miR-21 and miR-222 is adopted in the construction of tissue engineered nerves. The research results show that the present invention has good effects in the regulation of nerve growth factor (NGF) production, the promotion of axonal regeneration, the promotion of Schwann cell proliferation, and the regulation of angiogenesis, thus providing an appropriate microenvironment for peripheral nerve regeneration.

Furthermore, a Let-7 family miRNA inhibitor, miR-21, miR-222 or a mimetic thereof is embedded in nanomicrospheres by a nanomicrosphere technology, and the nanomicrospheres are bound to a chitosan tube or a silk fibroin tube to form a novel tissue-engineered nerve graft that is tublized and sutured in peripheral nerve defects and can regulate the expression of microRNAs through slow release locally in vivo.

The tublization system for promoting the peripheral nerve regeneration of the present invention is a tissue engineered nerve that is formed by, on the basis of a chitosan or silk fibroin tube developed in an early stage of the present invention, embedding a Let-7 family miRNA inhibitor, miR-21, miR-222 or a mimetic thereof in nanomicrospheres by a nanomicrosphere technology, and binding the nanomicrospheres to the biological tube, and that is tublized and sutured in peripheral nerve defects and can regulate the expression of microRNAs through slow release locally in vivo after suture.

The specific technical solutions of the present invention are as follows.

Use of a MicroRNA gene in the construction of tissue-engineered nerves and repair of peripheral nerve defects is provided, in which the MicroRNA gene is one or more of miRNAs of Family Let-7, miR-21 or miR-222. The members of Family Let-7 include let-7a, 7b, 7c, 7d, 7e, 7f, 7i and miR-98.

The peripheral nerve regeneration can be promoted by regulating the expression of the above microRNA genes, that is, by inhibiting the expression of Let-7 microRNAs or by up-regulating the expression of miR-21 or miR-222 to construct tissue-engineered nerves.

Preferably, a Let-7 family miRNA inhibitor, miR-21, miR-222 or a mimetic thereof may be coated or adsorbed as an ingredient for promoting the peripheral nerve regeneration to an outer and/or internal surface or pores of a tissue engineered nerve graft.

Preferably, the Let-7 family miRNA inhibitor, miR-21, miR-222 or a mimetic thereof is present on the tissue engineered nerve graft material in an amount of 10 μg/g-10 mg/g.

In a preferred technical solution of the present invention, the Let-7 family miRNA inhibitor, miR-21 or miR-222 or a mimetic thereof is embedded in nanomicrospheres by a nanomicrosphere technology. The nanomicrospheres may be polymeric nanomicrospheres carrying the Let-7 family miRNA inhibitor, miR-21, miR-222 or a mimetic thereof. Preferably, the polymeric material is composed of biocompatible fibronectin and heparin, and the weight ratio of fibronectin to heparin is 1:10-1:1.

Further preferably, the nanomicrosphere has an average diameter of 100-250 nm.

The nanomicrospheres are prepared through the following process.

An appropriate amount of fibronectin is dissolved in sterilized pure water to obtain a 1 mg/ml aqueous fibronectin solution. An appropriate amount of heparin is also dissolved in sterilized water to form a 1 mg/ml aqueous heparin solution. The aqueous fibronectin solution is then added to the aqueous heparin solution with stirring, and the reaction is continued at room temperature for 90 min. After the reaction is completed, the biocompatible crosslinking agent Genipin is added to the above solution, mixed until uniform, and reacted overnight at 4° C. to form light blue nanomicrospheres with uniform particle size, in which the weight ratio of Genipin to fibronectin is 1:5.

A MicroRNA is dissolved in saline to form a solution containing 250 ng/mL microRNA. The solution is then added to the above-mentioned nanomicrosphere solution, fully stirred and mixed at 4° C., and incubated for 2 hrs, to finally form a dispersion containing fibronectin-heparin nanomicrospheres carrying a microRNA gene for later use.

The Let-7 family miRNA inhibitor, miR-21, miR-222 or a mimetic thereof in the present invention is preferably

```
                                     (SEQ ID No: 1)
rno-let-7a-5p:    UGAGGUAGUAGGUUGUAUAGUU;

(SEQ ID No: 2)
rno-let-7a-3p:    CUAUACAAUCUACUGUCUUUCC;

(SEQ ID No: 3)
rno-let-7b-5p:    UGAGGUAGUAGGUUGUGUGGUU;

(SEQ ID No: 4)
rno-let-7b-3p:    CUAUACAACCUACUGCCUUCCC;
```

-continued

```
rno-let-7c-5p:        UGAGGUAGUAGGUUGUAUGGUU;
                                              (SEQ ID No: 5)

rno-let-7c-3p:        CUGUACAACCUUCUAGCUUUCC;
                                              (SEQ ID No: 6)

rno-let-7d-5p:        AGAGGUAGUAGGUUGCAUAGUU;
                                              (SEQ ID No: 7)

rno-let-7d-3p:        CUAUACGACCUGCUGCCUUUCU;
                                              (SEQ ID No: 8)

rno-miR-98-5p:        UGAGGUAGUAAGUUGUAUUGUU;
                                              (SEQ ID No: 9)

rno-miR-98-3p:        CUAUACAACUUACUACUUUCC;
                                              (SEQ ID No: 10)

rno-miR-21-5p:        UAGCUUAUCAGACUGAUGUUGA;
                                              (SEQ ID No: 11)

rno-miR-21-3p:        CAACAGCAGUCGAUGGGCUGUC;
                                              (SEQ ID No: 12)

rno-miR-222-5p:       GGCUCAGUAGCCAGUGUAGAU;
and                                           (SEQ ID No: 13)

rno-miR-222-3p:       AGCUACAUCUGGCUACUGGGU.
                                              (SEQ ID No: 14)
```

Another object of the present invention is to provide a tissue engineered nerve graft, in which an outer and/or internal surface or pores of the tissue engineered nerve graft are coated or adsorbed with one or more of a Let-7 family miRNA inhibitor, miR-21, miR-222 or a mimetic thereof. Preferably, the outer and/or internal surface or pores of the tissue engineered nerve graft are coated or adsorbed with polymeric nanomicrospheres of the Let-7 family miRNA inhibitor, miR-21, miR-222 or a mimetic thereof. The polymeric material is composed of biocompatible fibronectin and heparin. Preferably, the weight ratio of fibronectin to heparin is 1:10-1:1. Further preferably, the nanomicrospheres have an average diameter of 100-250 nm.

The tissue engineered nerve graft may be a tissue engineered nerve graft routinely used in the art, preferably a nerve graft scaffold or a nerve tube, where the scaffold or tube has pores distributed therein. Preferred is chitosan artificial nerve graft, a porous and highly tensile nerve tube with a scaffold having a porosity of 50%-90% and a pore size of 10-100 μm.

The present invention has the following advantages.

The present invention is designed according to the theoretical characteristics of peripheral nerve regeneration, in which a Let-7d miRNA inhibitor, miR-21, miR-222 or a mimetic thereof is applied in tissue engineered nerves. The present invention has effects in the regulation of nerve growth factor (NGF) production, the promotion of axonal regeneration, the promotion of Schwann cell proliferation, and the regulation of angiogenesis, thus providing an appropriate microenvironment for peripheral nerve regeneration. The Let-7d miRNA inhibitor, miR-21, miR-222 or a minetic thereof is embedded in nanomicrospheres composed of biocompatible fibronectin and heparin by a nanomicrosphere technology. The fibronectin and cell surface receptors for collagen, heparin, cellulose and integrin family are involved in a variety of cellular biological processes such as cell adhesion, migration, thrombosis and embryo differentiation. In the present invention, fibronectin and heparin are crosslinked to produce nanomicrospheres by using their biological characteristics, through which not only the stability of the Let-7 family miRNA inhibitor, miR-21, miR-222, or a mimetic thereof is increased, but also the sustained release is achieved to maintain the concentration locally in the site of nerve injury, and the cell proliferation, tissue or organ repair and regeneration are promoted. The nanomicrospheres of the present invention have good biocompatibility and stable biochemical properties, can effectively promote the proliferation of primary Schwann cells cultured in vitro, and have anti-apoptotic effect on neuronal cells. In vivo experiments demonstrate that the bridging of the tissue engineered nerve graft can facilitate the regeneration of peripheral nerves, thus being useful in the treatment of peripheral nerve injury.

DETAILED DESCRIPTION

Figure 1:
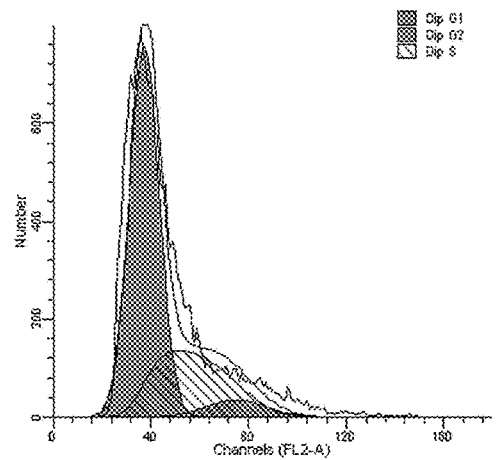
FIG. 1 shows the results of in vitro proliferation promotion experiment of Schwann cells as detected by flow cytometry (A. Let-7d inhibitor nanomicrosphere group; B. miR-98 inhibitor nanomicrosphere group; C. miR-21 nanomicrosphere group; D. miR-222 nanomicrosphere group; E. non-nanomicrosphere group with the combination of Let-7d inhibitor, miR-98 inhibitor, miR-21 mimetic and miR-222 mimetic; and F. nanomicrosphere group with the combination of Let-7d inhibitor, miR -98 inhibitor, miR-21 mimetic and miR-222 mimetic).
Figure 1:
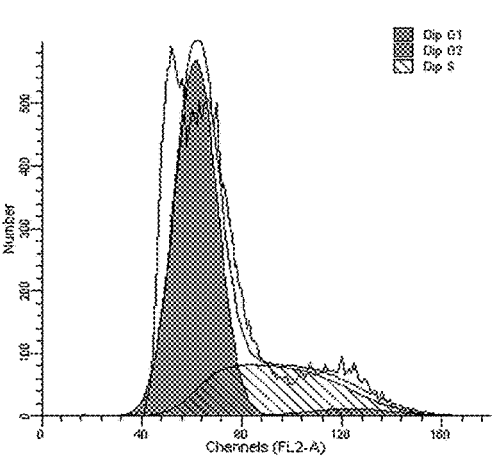
Figure 1:
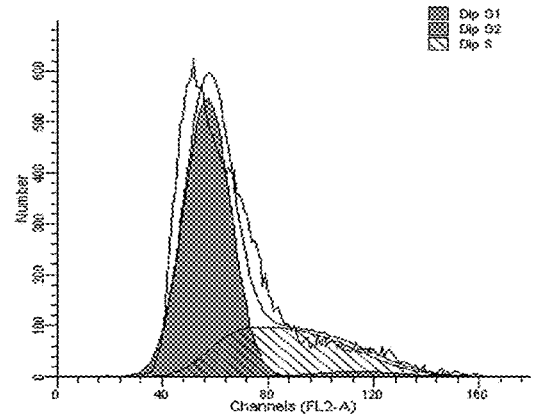
Figure 1:
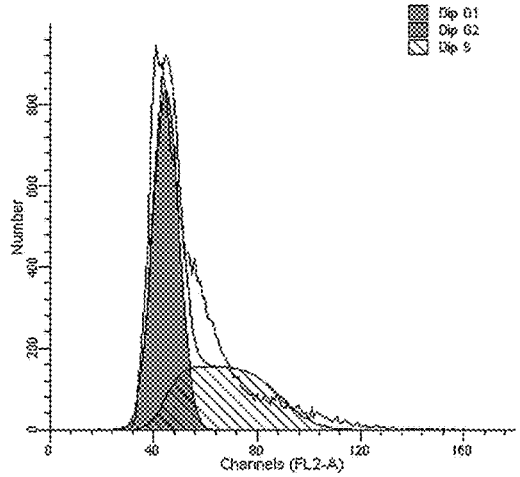
Figure 1:
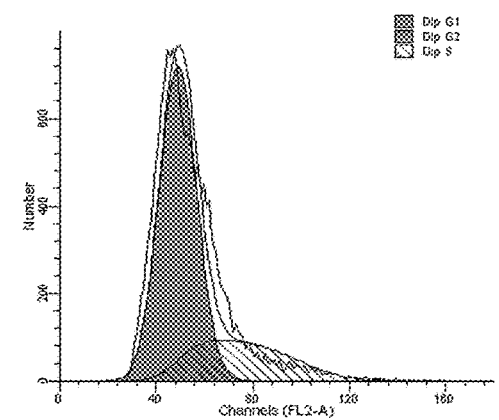
Figure 1:
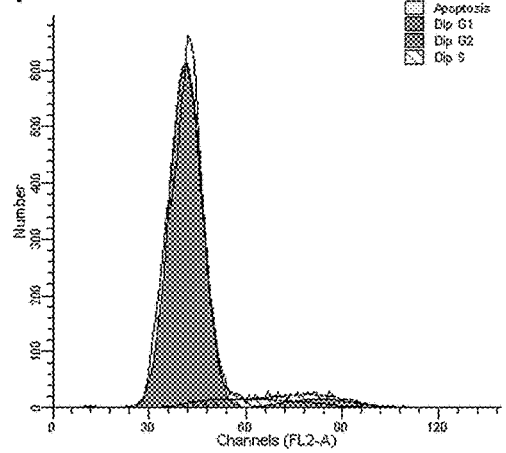

Specific steps of the present invention will be described by way of examples; however, the present invention is not limited thereto.

The terminology used in the present invention, unless otherwise specified, generally has the same meaning as commonly understood by one of ordinary skill in the art.

The present invention will now be described in further detail with reference to specific examples and accompanying drawings. It should be understood that the examples are merely illustrative of the present invention and not intended to limit the scope of the present invention in any way.

In the following examples, the various processes and methods not detailed herein are conventional methods known in the art.

The present invention will now be further described with reference to specific examples.

Example 1: Preparation of Nanomicrospheres Carrying a Let-7 Family miRNA Inhibitor, miR-21, miR-222 or a Minetic Thereof The Let-7 family miRNA inhibitor, miR-21, miR-222 or a minetic thereof has the following sequence:

| | |
|---|---|
| rno-let-7a-5p: | (SEQ ID No: 1) UGAGGUAGUAGGUUGUAUAGUU; |
| rno-let-7a-3p: | (SEQ ID No: 2) CUAUACAAUCUACUGUCUUUCC; |
| rno-let-7b-5p: | (SEQ ID No: 3) UGAGGUAGUAGGUUGUGUGGUU; |
| rno-let-7b-3p: | (SEQ ID No: 4) CUAUACAACCUACUGCCUUCCC; |
| rno-let-7c-5p: | (SEQ ID No: 5) UGAGGUAGUAGGUUGUAUGGUU; |
| rno-let-7c-3p: | (SEQ ID No: 6) CUGUACAACCUUCUAGCUUUCC; |
| rno-let-7d-5p: | (SEQ ID No: 7) AGAGGUAGUAGGUUGCAUAGUU; |
| rno-let-7d-3p: | (SEQ ID No: 8) CUAUACGACCUGCUGCCUUUCU; |
| rno-miR-98-5p: | (SEQ ID No: 9) UGAGGUAGUAAGUUGUAUUGUU; |
| rno-miR-98-3p: | (SEQ ID No: 10) CUAUACAACUUACUACUUUCC; |
| rno-miR-21-5p: | (SEQ ID No: 11) UAGCUUAUCAGACUGAUGUUGA; |
| rno-miR-21-3p: | (SEQ ID No: 12) CAACAGCAGUCGAUGGGCUGUC; |
| rno-miR-222-5p: and | (SEQ ID No: 13) GGCUCAGUAGCCAGUGUAGAU; |
| rno-miR-222-3p: | (SEQ ID No: 14) AGCUACAUCUGGCUACUGGGU. |

An appropriate amount of fibronectin was dissolved in sterilized pure water to obtain a 1 mg/ml aqueous fibronectin solution. An appropriate amount of heparin was also dissolved in sterilized water to form a 1 mg/ml aqueous heparin solution. The aqueous fibronectin solution was then added to the aqueous heparin solution with stirring, and the reaction was continued at room temperature for 90 min. After the reaction was completed, the biocompatible crosslinking agent Genipin was added to the above solution, mixed until uniform, and reacted overnight at 4° C. to form light blue nanomicrospheres with uniform particle size, in which the weight ratio of Genipin to fibronectin was 1:5.

One or more of the Let-7 family miRNA inhibitor, miR-21, miR-222 or a minetic thereof was dissolved in saline to form a solution containing 250 ng/mL of the Let-7 family miRNA inhibitor, miR-21, miR-222 or a minetic thereof. The solution was then added to the above-mentioned nanomicrosphere solution, fully stirred and mixed at 4° C., and incubated for 2 hrs, to finally form a dispersion containing fibronectin-heparin nanomicrospheres carrying the Let-7 family miRNA inhibitor, miR-21, miR-222 or a minetic thereof.

Example 2. Preparation of Tissue Engineered Nerves Load with Nanomicrospheres

A nerve tube was prepared following the method as described in Electrospun, Reinforcing Network-Containing, Silk Fibroin-Based Nerve Guidance Conduits for Peripheral Nerve Repair Journal of Biomaterials and Tissue Engineering Vol. 6, 53-60, 2016. The nerve tube was incubated for 2 hrs with the nanomicrospheres prepared in Example 1 at room temperature for physical adsorption, to obtain a tissue engineered nerve loaded with nanomicrospheres. Alternatively, the nerve tube was incubated for 2 hrs with one or more of the Let-7 family miRNA inhibitor, miR-21, miR-222 or a minetic thereof at room temperature for physical adsorption, to obtain a tissue engineered nerve directly loaded with the Let-7 family miRNA inhibitor, miR-21, miR-222 or a minetic thereof.

Tissue engineered nerve 1: tissue engineered nerve loaded with Let-7d inhibitor nanomicrospheres.

Tissue engineered nerve 2: tissue engineered nerve loaded with miR-98 inhibitor nanomicrospheres.

Tissue engineered nerve 3: tissue engineered nerve loaded with miR-21 minetic nanomicrospheres Tissue engineered nerve 4: tissue engineered nerve loaded with miR-222 minetic nanomicrospheres.

Tissue engineered nerve 5: tissue engineered nerve loaded with Let-7d inhibitor, miR-98 inhibitor, miR-21 minetic, and miR-222 minetic.

Tissue engineered nerve 6: tissue engineered nerve loaded with nanomicrospheres of Let-7d inhibitor, miR-98 inhibitor, miR-21 minetic, and miR-222 minetic.

Example 3: In Vitro Proliferation Promotion Experiment of Schwann Cells

Tissue engineered nerves 1-6 of 1 cm in length were totally immersed in 2 ml of a culture media (which is, depending on the experimental purposes, DMEM+10% FBS in the Schwann cell proliferation experiment; and 97% Neurobasal+2% B27+1% GluMAX in the apoptosis detection experiment of DRG neuron) for 24 hrs at room temperature respectively, and then stored at 4° C. for later use.

Newborn SD rats aged 1-2 days was frozen, and disinfected by spraying 75% alcohol, followed by the steps below which are conducted on a sterile ultraclean bench in a culture room. The sciatic nerve was removed by exposing it via the muscular space posterolateral to the femur and then placed in a pre-cooled HBSS solution. After the epineurium was peeled off under a dissecting microscope, the sciatic nerve was placed in a 1.5 ml EP tube containing 200 µl of 1 mg/ml collagenase, and digested at 37° C. for 30 min. Then, the collagenase was removed, and 0.125% trypsin was added, for digestion at 37° C. for 12 min. The digested solution was transferred to a 5 ml EP tube, 3 ml Schwann cell culture medium was added and pipetted repeatedly until substantially no tissue mass was visible. After centrifugation, the supernatant was discarded. The pellet was washed twice with a Schwann cell culture medium, then inoculated at a density of 1×10$^6$ cells in a plate previously coated with PLL, and placed in a humidified incubator at 37° C. with 95% air and 5% CO$_2$. The culture medium was refreshed with a cytosine arabinoside containing medium (1:1000) in 24 hrs. After 24 hrs, the culture medium was refreshed with a medium containing 2 µM forsokolin and 10 ng/ml HRG, and refreshed once every 3 days. After the cells were grown to 50% confluent, the culture medium was refreshed completely with a leachate of tissue engineered nerves 1-6 respectively, and continuously cultured for 24 hrs. After digestion with 0.25% trypsin, the cell density was adjusted to 5×10$^5$/ml. 0.5 ml of 50 ug/ml PI staining solution was added, and the cells were stained for 30 min at room temperature in the dark. The cell cycle was detected by flow cytometry following a standard procedure The detection results by flow cytometry are shown in FIG. 1 (A. Let-7d inhibitor nanomicrosphere group; B. miR-98 inhibitor nanomicrosphere group; C. miR-21 nanomicrosphere group; D. miR-222 nanomicrosphere group; E. non-nanomicrosphere group with the combination of Let-7d inhibitor, miR-98 inhibitor, miR-21 mimetic and miR-222 mimetic; and F. nanomicrosphere group with the combination of Let-7d inhibitor, miR-98 inhibitor, miR-21 mimetic and miR-222 mimetic). The results show that 74.93% and 88.58% of the Schwann cells in the experimental groups E and F are in the proliferation cycle, which is significantly higher than the 64.71% in FIG. 1 Panel A, 68.57% in FIG. 1 Panel B, 66.34% in FIG. 1 Panel C, and 60.15% in FIG. 1 Panel D, suggesting that the effect of the combination of Let-7d inhibitor, miR-98 inhibitor, miR-21 mimetic and miR-222 mimetic is better than that of any one alone. Moreover, the tissue engineered nerve loaded with nanomicrospheres containing the Let-7d inhibitor, miR-98 inhibitor, and miR-21 and miR-222 mimetics has an obviously better effect on the Schwann cell proliferation than the tissue engineered nerve directly adsorbed with the Let-7d inhibitor, miR-98 inhibitor, and miR-21 and miR-222 mimetics. It is concluded that the tissue engineered nerve loaded with nanomicrospheres containing the combination of Let-7d inhibitor, miR-98 inhibitor, and miR-21 and miR-222 mimetics can promote the proliferation of primary Schwann cells cultured in vitro.

DRG L4, 5, and 6 from SD rat embryos of 16 days were digested with 0.25% trypsin at 37° C. for 15 min, and inoculated in a 24-well culture plate at a cell density of 10$^5$ cells/ml. After 1 day of conventional culture in vitro, it was found through observation under a phasecontrast microscope that cells adherent occurred and a few neurites were grown. After pretreatment with 40 ng/ml TNF-α for 12 hrs, the primary DRG neurons cultured were treated with a leachate of tissue engineered nerves 1-6 for 12 hrs respectively. The culture medium was aspirated off and the cells were washed once with 0.01 M PBS. 4% paraformaldehyde was added, and the cells were immobilized at room temperature for 30 min. The fixative was removed and the cells were washed for 10 min with 0.01 M PBS at room temperature (×3). The cells were blocked for 60 min at 37° C. with 0.01 M PBS containing 10% goat serum and 0.3% Triton X-0100, and then the blocking solution was aspirated off. The primary antibodies, i.e. the Rabbit antibodies against cleaved caspase-3 (1:500) and the Mouse rabbit antibody against total caspase-3 (1:800), were added dropwise and incubated overnight at 4° C. The cells were washed for 10 min with 0.01 M PBS (×3). The secondary antibodies, i.e. the TRITC labeled secondary antibody donkey anti-mouse IgG (1:600), and the FITC labeled secondary antibody donkey anti-rabbit IgG (1:600) were added dropwise, and the nucleus was labeled with Hoechst (5 µg/ml), stood for 1 hr at room temperature in the dark, and then washed for 10 min with 0.01 M PBS (×3). The immunofluorescence cytochemical detection results were observed under a laser confocal microscope (FITC excitation wavelength: 488 nm, and emission wavelength: 500-535 nm; and Hoechst Ar ion excitation wavelength: 353-364 nm, and emission wavelength: 460-480 nm).

Figure 2:
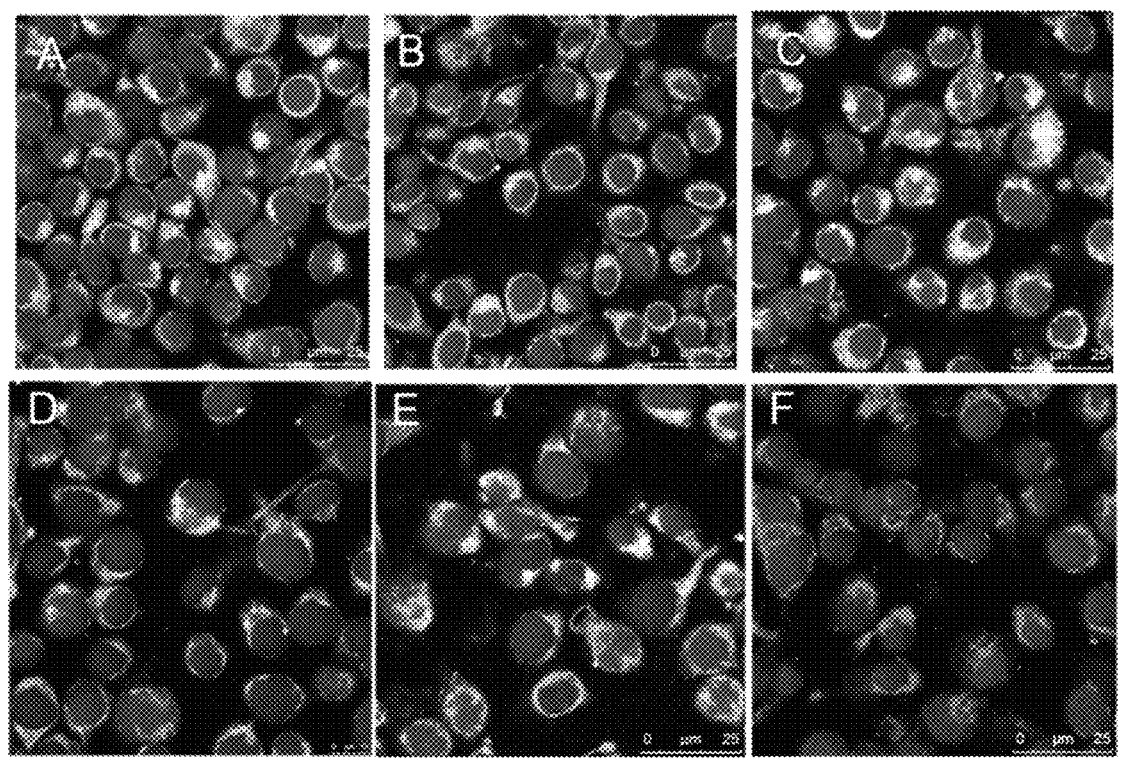
FIG. 2 shows the results of immunohistochemical staining for cells in anti-apoptotic experiment of primary dorsal root ganglion (DRG) neurons cultured in vitro (A. Let-7d inhibitor nanomicrosphere group; B. miR-98 inhibitor nanomicrosphere group; C. miR-21 nanomicrosphere group; D. miR-222 nanomicrosphere group; E. non-nanomicrosphere group with the combination of Let-7d inhibitor, miR-98 inhibitor, miR-21 mimetic and miR-222 mimetic; and F. nanomicrosphere group with the combination of Let-7d inhibitor, miR-98 inhibitor, miR-21 mimetic and miR-222 mimetic).

The immunohistochemical staining results of cells are shown in FIG. 2 (A. Let-7d inhibitor nanomicrosphere group; B. miR-98 inhibitor nanomicrosphere group; C. miR-21 nanomicrosphere group; D. miR-222 nanomicrosphere group; E. non-nanomicrosphere group with the combination of Let-7d inhibitor, miR-98 inhibitor, miR-21 mimetic and miR-222 mimetic; and F. nanomicrosphere group with the combination of Let-7d inhibitor, miR-98 inhibitor, miR-21 mimetic and miR-222 mimetic). In the figure, the blue indicates Hoechst labeled nucleus; the red indicates total caspase-3 which is expressed generally in all of the normal cells; the green indicates activated caspase-3, which is expressed merely in apoptotic cells. The results show that the immunohistochemistry of Let-7d inhibitor nanomicrosphere group (FIG. 2 Panel A), the miR-98 inhibitor nanomicrosphere group (FIG. 2 Panel B), the miR-21 nanomicrosphere group (FIG. 2 Panel C), and the miR-222 nanomicrosphere group (FIG. 2 Panel D) indicates the presence of a lot of green, that is, activated caspase-3, suggesting the apoptosis of cells. FIG. 2 Panel E shows the result of the non-nanomicrosphere group with the combination of Let-7d inhibitor, miR-98 inhibitor, miR-21 mimetic and miR-222 mimetic. Although activated caspase-3 is still expressed, the level is obviously lower than that of the experimental group with a single MicroRNA. FIG. 2 Panel F shows the result of the nanomicrosphere group with the combination of Let-7d inhibitor, miR-98 inhibitor, miR-21 mimetic and miR-222 mimetic. The result shows that no activated caspase-3 is expressed, suggesting that almost no apoptosis of cells occurs. It is concluded that the tissue engineered nerve with the combination of Let-7d inhibitor, miR-98 inhibitor, and miR-21 and miR-222 mimetics can greatly inhibit the apoptosis caused by TNF-a of primary DRG neurons cultured.

Example 4. Use of MicroRNA Gene-Meditated Novel Tissue Engineered Nerve in the Repair of Nerve Defects 1. Grouping of Animal Experiment and Model Preparation 1.1. Animal Experiment and Grouping The rats were randomly divided into 4 groups (each group having 15 animals), including a tissue engineered nerve group (experimental group with tissue-engineered nerve 6 described in Example 2), an autologous nerve group, a chitosan nanomicrosphere-loaded tube group (negative control group), and a sham operation group (normal group).

Preparation of chitosan nanomicrosphere-loaded tube:

As described in Kawadkar J, Chauhan M K. I Intra-articular delivery of genipin cross-linked chitosan nanomicrospheres of flurbiprofen: preparation, characterization, in vitro and in vivo studies. [J]. *European Journal of Pharmaceutics and Biopharmaceutics*, 2012,81(3):563-572, 3 ml of a 30 g/L chitosan solution in acetic acid/water was added dropwise to 40 ml of liquid paraffin containing 20 g/L span-80 and magnetically stirred at room temperature to form a stable W/O emulsion system. Biological cross-linking agent Genipin with 2 ml volume fraction of 70% ethanol solution dissolved, into the emulsion for crosslinking curing. After completion of the reaction, the resulting chitosan nanomicrospheres were collected by centrifugal dispersion. The biocompatible crosslinking agent Genipin was dissolved in 2 ml of a 70 vol % ethanol solution, and added dropwise into the emulsion for curing by crosslinking. After completion of the reaction, the resulting chitosan nanomicrospheres were collected by centrifugation. The Let-7d inhibitor, miR-98 inhibitor, miR-21 and miR-222 mimics described in Example 1 were dissolved in physiological saline to form a 250 ng/mL solution containing the Let-7d inhibitor, miR-98 inhibitor, miR-21 and miR-222 mimics. The solution was then added to the above-mentioned nanomicrosphere solution, mixed fully by stirring at 4° C., and incubated for 2 hrs to finally form a dispersion of chitosan nanomicrospheres carrying the Let-7d inhibitor, miR-98 inhibitor and miR-21 and miR-222 mimetics.

A nerve tube was prepared following the method described in Electrospun, Reinforcing Network-Containing, Silk Fibroin-Based Nerve Guidance Conduits for Peripheral Nerve Repair *Journal of Biomaterials and Tissue Engineering* Vol. 6, 53-60, 2016. The nerve tube was incubated for 2 hrs with the nanomicrospheres for physical adsorption, to obtain a chitosan tube loaded with nanomicrospheres.

1.2. Model Preparation

The animals were intraperitoneally anesthetized with a compound anesthetic (0.2-0.3 ml/100 g body weight). After the success of anesthesia, conventional skin preparation, disinfection, and draping were done in a surgical area at the left femur. An incision was made right in the center posterior to the left femur, followed by cutting the skin and fascia, to free and fully expose the sciatic nerve. The sciatic nerve was dissected in the middle of the femur and a 10 mm defect was caused. For the tissue engineered nerve group (TENG) and the fibroin tube group (Scaffold), the dissected ends at both sides of the nerve were inserted 1 mm into the tube, and immobilized by suturing the epineurium with an atraumatic suture. For the autologous nerve group, the dissected sciatic nerve was reversed before suturing. The incision was conventionally closed. The model preparation and subsequent feeding and observation were all carried out in an SPF barrier system.

2. Evaluation of Postoperative Functional Recovery 2.1. Test of Electrophysiological Functions 12 weeks after operation, the rats were subjected to electrophysiological examination at room temperature. The rats were weighed and intraperitoneally injected with compound anesthetic (0.2-0.3 ml per 100 g body weight of rat). After the success of anesthesia, the sciatic nerve was exposed and carefully separated with a glass dissecting needle. The compound muscle action potentials (CMAPs) were recorded. The recording electrode was inserted into the muscle belly of the gastrocnemius muscle, and the interference electrode was placed on the skin surface of the rat knee. The stimulation electrodes were sequentially placed proximal and distal to the sciatic nerve trunk of the injured site to stimulate the nerve. The CMAPs were recorded and the amplitude and latency of the CMAPs were measured. Similarly, the amplitude and latency of the CMAPs at the normal side were recorded. The amplitude of CMAPs is proportional to the nerve fibers that dominate the target muscle. Therefore, the detection of CMAPs provides an important parameter for the recovery of the conduction function of peripheral nerves. The CMAP recovery index was calculated according to the formula: recovery index =maximal amplitude of CMAPs at the operated side/maximal amplitude of CMAPs at the normal side.

Figure 3:
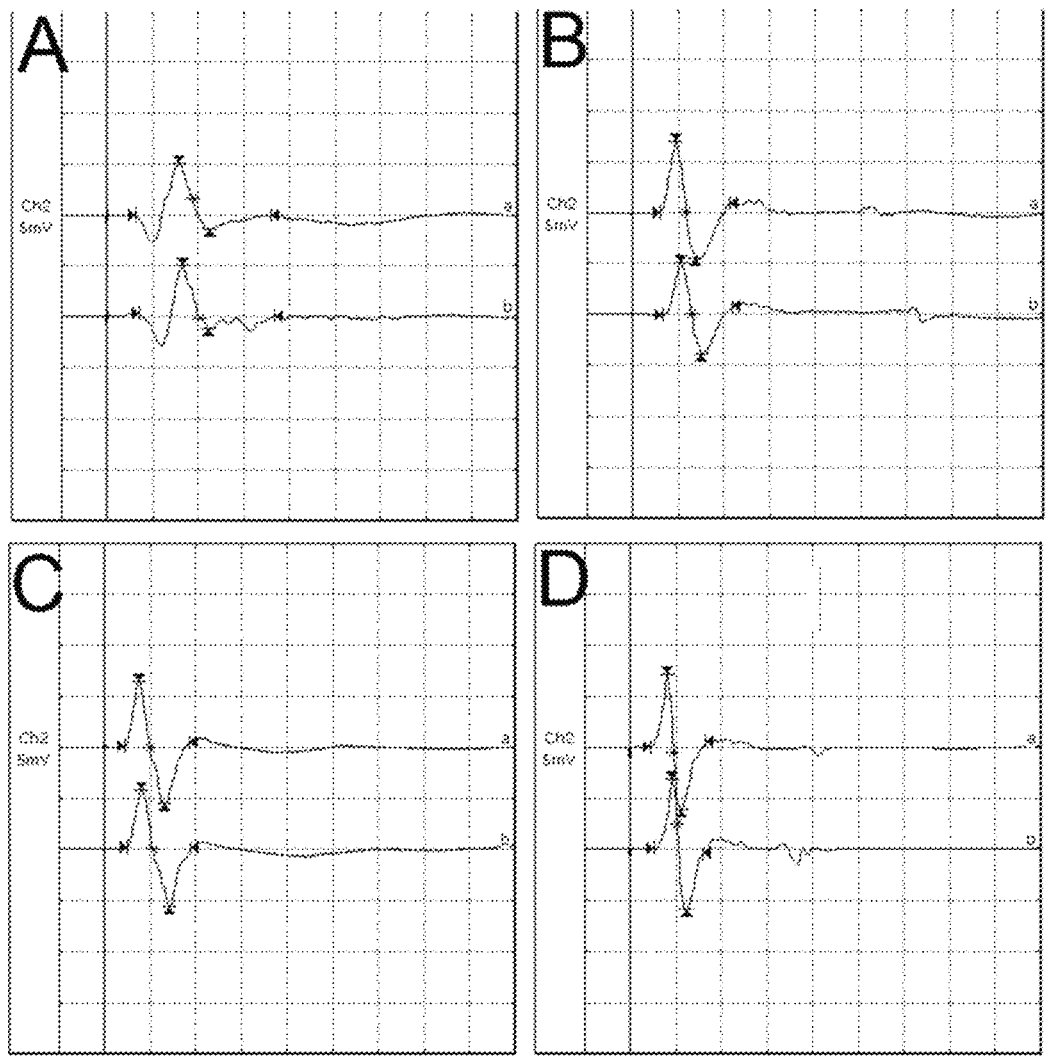
FIG. 3 shows the results of electrophysiological function detected in the experiment of repairing rats having nerve defects with the MicroRNA gene mediated novel tissue engineered nerve of the present invention (A. chitosan nanomicrosphere-loaded tube group; B. experimental group with tissue engineered nerve 6 of the present invention; C. autologous nerve group; and D. normal group).

The experimental results are shown in FIG. 3 (A. chitosan nanomicrosphere-loaded tube group; B. experimental group with tissue engineered nerve 6 of the present invention; C. autologous nerve group; and D. normal group). The results show that the recovery of CMAP and nerve conduction velocity in the gastrocnemius muscle of the rats in the experimental group with tissue engineered nerve 6 of the present invention is significantly better than that of the chitosan nanomicrosphere group, and is close to that of the positive control autologous nerve group.

2.3. Perfusion Fixation and Acquisition of Tissue 2.3.1. Perfusion Fixation

At weeks 4 and 12 after surgery, rats were given an operation with a compound anesthetic and the chest was opened to expose the heart. The right auricle was pierced, and the needle was pierced into the left ventricle to perfuse it with physiological saline (where the perfusion volume was about 2 times of the body weight) until the color of the liver became light, and the fluid in the mesenteric vessels became nearly colorless from the red. Then, equal volume of 4% paraformaldehyde was perfused.

2.3.2. Acquisition of Tissue

Three rats in each group were perfused and fixed. The regenerated sciatic nerve trunk was removed, immersed in a pre-cooled glutaraldehyde fixative solution, and left for being embedded with a resin and observed under an electron microscope.

After perfusion, the bilateral gastrocnemius muscles with a volume of about 0.5 cm×0.3 cm×0.3 cm were carefully dissected and cut intact, and immersed overnight in a suitable amount of a pre-cold post-fixative solution (4% PA) at 4° C. The regenerated sciatic nerve trunk on the operated side was carefully dissected and removed, and a segment of sciatic nerve in a corresponding site at the normal side was removed and taken as the control. The sciatic nerve sample was straightly attached on a cardboard and immersed overnight in a suitable amount of a pre-cold post-fixative solution (4% PA) at 4° C.

2.4. Sample Treatment and Observation 2.4.1. Treatment of Samples for Electron Microscopy At weeks 4 and 12 after operation, the sciatic nerve and gastrocnemius muscle samples were fixed with glutaraldehyde, followed by post-fixation with 1% osmic acid, fast staining with uranyl acetate, dehydration over ethanol gradient, and embedding in Epon 812 epoxy resin.

2.4.2. Masson Trichrome (MT) Staining for Muscles

At weeks 4 and 12 after operation, the gastrocnemius muscle was precipitated in a sucrose solution, then embedded in 5% sucrose (formulated in 0.1 M PB), frozen, and laterally sliced into 10 μm. The slices were placed at room temperature for about 24 hours, for facilitating the tissue attachment. Masson trichrome staining was performed as follows. The collagen fibers appeared blue, the muscle fibers appeared red and the nuclei appeared black and blue.

(1) The slices were placed in ddH$_2$O for 3-5 min.

(2) The slices were stained with Ehrlich hematoxylin for 20 min.

(3) The slices were immersed in ddH$_2$O for about 1 min, and amenable to color separation for about 1min in 1% hydrochloric acid in ethanol.

(4) Bluing with tap water is continued for about 20 min under a microscope.

(5) The slices were stained with Ponceau S—acid complex red for 5 min.

(6) The slices were washed with ddH$_2$O.

(7) The slices were stained with 1% phosphomolybdic acid.

(8) The slices were directly stained with toluidine blue for 5 min without washing with water.

(9) The slices were washed with ddH$_2$O, and amenable to color separation for about 1 min with 1% glacial acetic acid.

(10) The slices were dehydrated with 95% ethanol for 5 min (×3), followed by dehydration in absolute ethanol for 5 min (×2).

(11) The slices were transparented with xylene for 5 min (×3), mounted with resin, air dried at room temperature, and then observed under an optical microscope.

Figure 4:
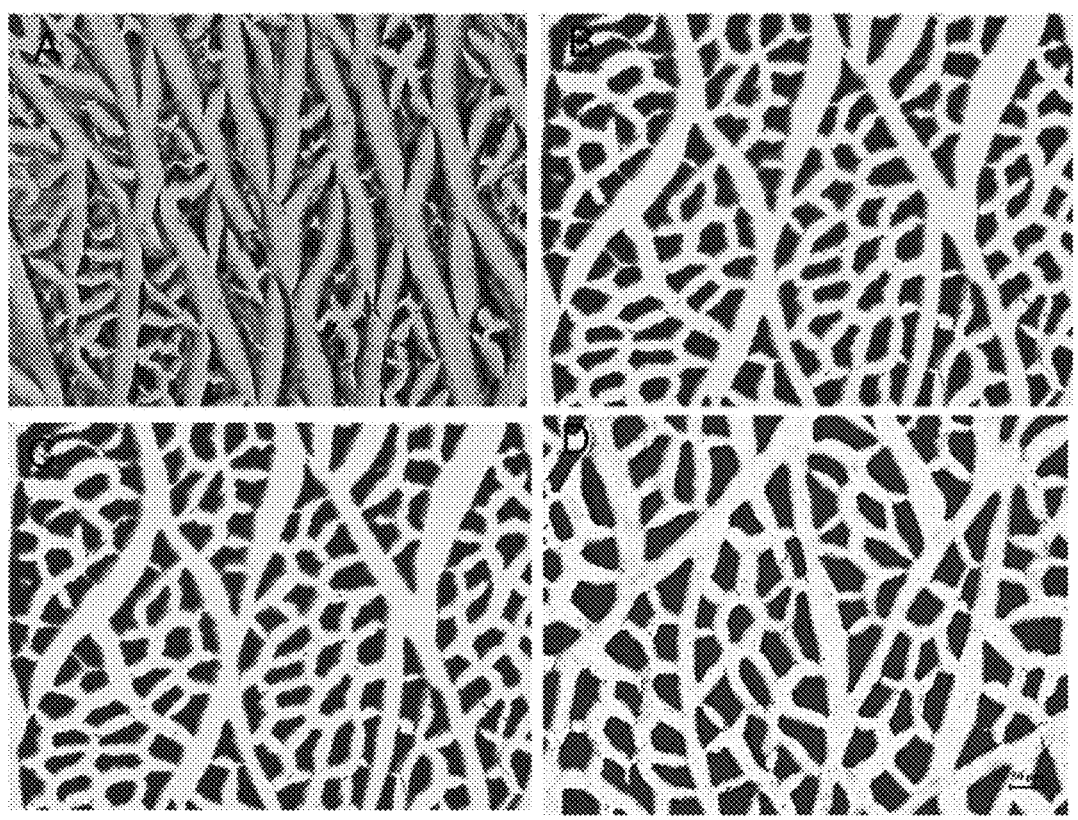
FIG. 4 shows the results of Masson Trichrome (MT) staining for muscles in the experiment of repairing rats having nerve defects with the MicroRNA gene mediated novel tissue engineered nerve of the present invention (A. chitosan nanomicrosphere-loaded tube group; B. experimental group with tissue engineered nerve 6 of the present invention; C. autologous nerve group; and D. normal group).

The experimental results are shown in FIG. 4 (A. chitosan nanomicrosphere-loaded tube group;

B. experimental group with tissue engineered nerve 6 of the present invention; C. autologous nerve group; and D. normal group, where the red indicates muscle fiber; and the blue indicates collagen fiber). The results show that the cross-sectional area of the muscle fibers in the experimental group with tissue engineered nerve 6 of the present invention is close to that of the autologous nerve group, both of which is significantly higher than that of the chitosan nanomicrosphere group; and the percent of area of the collagen fibers is significantly lower than that of the chitosan nanomicrosphere group.

2.5. Electron Microscopic Analysis of Nerve Tissue (1) Harris hematoxylin: 0.5 g of hematoxylin was added to and dissolved in 5 ml of absolute ethanol. 10 g of potassium aluminum sulfate was added to and dissolved in 100 ml of double distilled water. The two solutions were mixed until uniform and heated to boiling. Then, 0.25 g of mercury oxide yellow was added, and cooled in ice water after dissolution. After filtering, 5 ml of glacial acetic acid was added. (2) Trichrome stain solution: 0.3 g of solid green FCF, 0.6 g of chromotrope 2R and 0.6 g of phosphotungstic acid were added in sequence to and dissolved in 100 ml of double distilled water, and then 2 ml of glacial acetic acid was added to adjust the pH to 3.4. The stain solution might be stored at room temperature for two weeks. If the preservation time is too long or the pH value changes, the color shifts towards purple and the green become lighter. (3) The 0.3% glacial acetic acid solution was formulated immediately before use.

Referring to the experimental method of Meyer et al with modification, the slices were (1) conventionally deparaffinized into ddH$_2$O; (2) stained with Harris hematoxylin for 5 min; (3) washed for 5 min with double distilled water, and controlled in terms of bluing under a microscope; (4) stained with the trichrome stain solution for 30 min; (5) washed twice with 0.3% glacial acetic acid for 20 seconds each; and washed for 5-10 min with running water, until the color of the tissue slice was unchanged; and (7) dehydrated, transparented, and mounted with resin.

Figure 5:
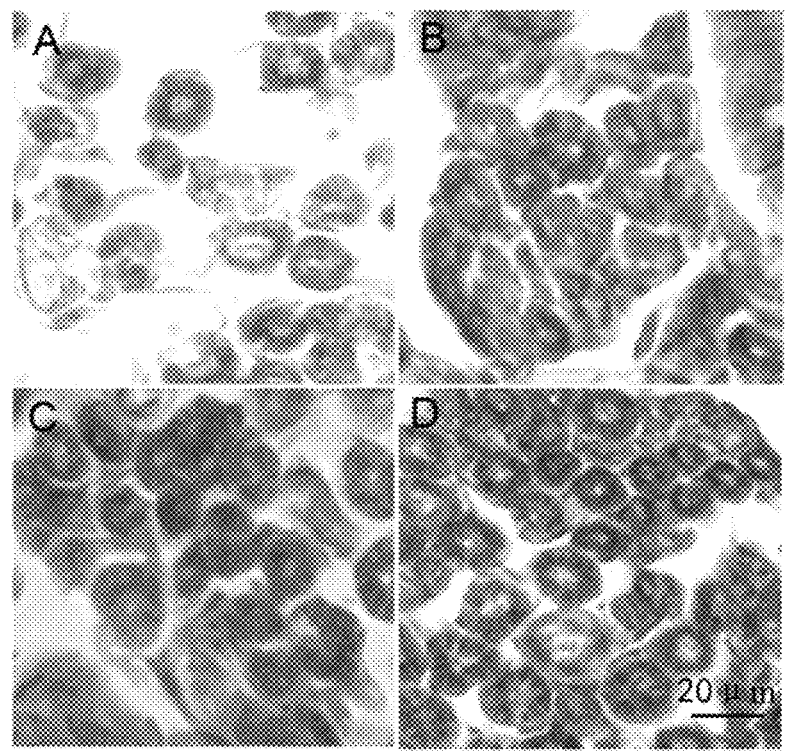
FIG. 5 shows the results under optical microscope of trichrome staining for nerves in regenerated nerve trunk in the experiment of repairing rats having nerve defects with the MicroRNA gene mediated novel tissue engineered nerve of the present invention (A. chitosan nanomicrosphere-loaded tube group; B. experimental group with tissue engineered nerve 6 of the present invention; C. autologous nerve group; and D. normal group).

The results are shown in FIG. 5 (A. chitosan nanomicrosphere-loaded tube group; B. experimental group with tissue engineered nerve 6 of the present invention; C. autologous nerve group; and D. normal group, where the purple indicates Schwann cell nuclei; and the green indicates the nerve axon). The results show that the formation of myelin sheath of the regenerated nerve trunk in the experimental group with tissue engineered nerve 6 of the present invention is significantly better than that of the chitosan nanomicrosphere group, and is close to that of the positive control autologous nerve group.

3. Data Statistics

In this study, the data of group design and morphometric analysis was analyzed by one-way ANOVA using the STATA7 statistical analysis software. If the difference between the groups was statistically significant, the Turkey's method was used to compare pairwise. The results are expressed as mean±standard deviation (X±SD), and $p<0.05$ indicates that the difference was statistically significant.

The invention claimed is:

1. A method for construction of a tissue engineered nerve or repair of peripheral nerve defects, comprising administering a Let-7 family miRNA inhibitor, miR-222, or a mimetic thereof to a tissue engineered nerve graft.

2. The method according to claim 1, further comprising: depositing the Let-7 family miRNA inhibitor, miR-222, or a mimetic thereof on an surface of the tissue engineered nerve graft, wherein the surface is an outer surface, an inter surface, a surface of a pore in the tissue engineered nerve graft, or a mixture thereof.

3. The method according to claim 2, wherein the Let-7 family miRNA inhibitor, miR-222, or a mimetic thereof is present on the tissue engineered nerve graft material in an amount of 10 μg/g-10 mg/g.

4. The method according to claim 1, further comprising embedding the Let-7 family miRNA inhibitor, miR-222, or a mimetic thereof in nanomicrospheres.

5. The method according to claim 4, wherein the embedded nanomicrospheres are polymeric nanomicrospheres carrying the Let-7 family miRNA inhibitor, miR-222, or a mimetic thereof, and the polymeric material is composed of biocompatible fibronectin and heparin.

6. The method according to claim 5, wherein the weight ratio of fibronectin to heparin is 1:10-1:1.

7. The method according to claim 1, wherein the Let-7 family miRNA inhibitor, miR-222, or a mimetic thereof is:

```
                                      SEQ ID No: 1;
rno-let-7a-5p: UGAGGUAGUAGGUUGUAUAGUU, SEQ ID No: 2;
rno-let-7a-3p: CUAUACAAUCUACUGUCUUUCC, SEQ ID No: 3;
rno-let-7b-5p: UGAGGUAGUAGGUUGUGUGGUU, SEQ ID No: 4;
rno-let-7b-3p: CUAUACAACCUACUGCCUUCCC, SEQ ID No: 5;
rno-let-7c-5p: UGAGGUAGUAGGUUGUAUGGUU, SEQ ID No: 6;
rno-let-7c-3p: CUGUACAACCUUCUAGCUUUCC, SEQ ID No: 7;
rno-let-7d-5p: AGAGGUAGUAGGUUGCAUAGUU, SEQ ID No: 8;
rno-let-7d-3p: CUAUACGACCUGCUGCCUUUCU,
```

-continued
```
                                      SEQ ID No: 9;
rno-miR-98-5p: UGAGGUAGUAAGUUGUAUUGUU, SEQ ID No: 10;
rno-miR-98-3p: CUAUACAACUUACUACUUUCC, SEQ ID No: 13;
rno-miR-222-5p: GGCUCAGUAGCCAGUGUAGAU,
and SEQ ID No: 14;
rno-miR-222-3p: AGCUACAUCUGGCUACUGGGU.
```

8. A tissue engineered nerve graft, wherein a Let-7 family miRNA inhibitor, miR-222, or a mimetic thereof is deposited on an surface of the tissue engineered nerve graft and the surface is an outer surface, an inter surface, a surface of a pore in the tissue engineered nerve graft, or a mixture thereof.

9. The tissue engineered nerve graft according to claim 8, wherein:
the Let-7 family miRNA inhibitor, miR-222, or a mimetic thereof is embedded in nanomicrospheres;
the embedded nanomicrospheres are polymeric nanomicrospheres; and
the polymeric material is composed of biocompatible fibronectin and heparin.

* * * * *